United States Patent
Brown et al.

(10) Patent No.: US 6,673,371 B2
(45) Date of Patent: Jan. 6, 2004

(54) SHEAR GEL COMPOSITIONS

(75) Inventors: Charles Rupert Brown, Bedford (GB); Peter Simon Carew, Wirral (GB); John Charles Eklund, Wirral (GB); Jeannette Marcia Evans, Bedford (GB); Peter Fairley, Le Meux (FR)

(73) Assignee: Unilever Home & Personal Care USA, division of Conopco, Inc., Chicago, IL (US)

( * ) Notice: Subject to any disclaimer, the term of this patent is extended or adjusted under 35 U.S.C. 154(b) by 63 days.

(21) Appl. No.: 10/038,221

(22) Filed: Oct. 24, 2001

(65) Prior Publication Data

US 2002/0085987 A1 Jul. 4, 2002

(30) Foreign Application Priority Data

Oct. 30, 2000 (GB) ................................. 0026473

(51) Int. Cl.[7] ............................. A61K 9/14; A61K 7/06; A61K 7/11
(52) U.S. Cl. ...................... 424/486; 424/484; 424/489; 424/70.1; 424/70.4; 424/70.11; 424/70.12; 424/70.13; 424/70.14
(58) Field of Search ............... 424/70.1, 70.4, 424/70.11, 70.12, 70.13, 70.14, 484, 486, 489

(56) References Cited

U.S. PATENT DOCUMENTS

| 5,089,269 A | 2/1992 | Noda et al. |
| 5,217,741 A | 6/1993 | Kawachi et al. |
| 5,286,405 A | 2/1994 | Rennie et al. |
| 5,635,171 A | 6/1997 | Nadaud |
| 5,641,480 A | 6/1997 | Vermeer |
| 5,726,138 A | 3/1998 | Tsaur et al. |
| 5,738,897 A | 4/1998 | Gidley et al. |

FOREIGN PATENT DOCUMENTS

| DE | 199 33 452 | 2/2000 |
| EP | 0 250 623 | 1/1988 |
| EP | 0316054 | 5/1989 |
| EP | 0 355 908 | 2/1990 |
| EP | 0 590 538 A1 | * 9/1993 |
| EP | 0590538 A1 | 4/1994 |
| EP | 0 630 580 A2 | 12/1994 |
| GB | 2 188 060 A | 9/1987 |
| WO | 95/12988 | 5/1995 |
| WO | 98/08601 | 3/1998 |
| WO | 98/11877 | 3/1998 |
| WO | 99/51716 | * 3/1998 |
| WO | 98/08601 | 4/1998 |
| WO | 99/26585 | 6/1999 |
| WO | 99/51193 | * 10/1999 |
| WO | 99/51716 | 10/1999 |

OTHER PUBLICATIONS

International Search Report Application No. PCT/EP/01/11775 mailed Apr. 16, 2002.
Patent Abstracts of Japan, vol. 2000, No. 12, & JP 2000 239147 A (Naris Cosmetics Co., Ltd.
Search Report under Section 17, Application No. GB 0026473.9 dated Apr. 23, 2001.

* cited by examiner

*Primary Examiner*—Thurman K. Page
*Assistant Examiner*—Humera N. Sheikh
(74) *Attorney, Agent, or Firm*—Michael P. Aronson

(57) ABSTRACT

A composition which has a thickened fluid form comprises:

(i) a first (shear gel) phase comprising at least one polymer which is capable of forming a gel, which polymer is present in the composition as a shear gel (i.e., a multiplicity of separate gel particles which have been formed by subjecting the polymer to shear while gel formation takes place); and (ii) a second (encapsulated) phase which is in the form of particles or droplets which comprise a hair benefit agent and are entrapped by the gel matrix of at least a proportion of the gel particles.

The composition may allow enhanced delivery of the encapsulated phase.

13 Claims, 6 Drawing Sheets

SHEAR GEL COMPOSITIONS

FIELD OF THE INVENTION

This invention relates to compositions having a thickened fluid form, to a process for their production and to their use. In particular, the invention relates to compositions comprising a phase formed from a particular type of gel which may be used, for example, as hair treatment compositions and personal wash compositions.

BACKGROUND AND PRIOR ART

Suspending agents are commonly employed in a variety of different types of compositions (eg, in hair treatment compositions) in order to improve stability against separation of the components, especially settling of suspended materials.

Examples of suspending agents commonly used in hair treatment compositions include crystalline suspending agents (such as ethylene glycol distearate) and inorganic structurants (such as swelling clays). Although these materials are effective for suspending particulate matter, they can adversely affect lathering performance and impart an undesirable cloudy appearance to the composition. Furthermore, during use of the composition they tend to get co-deposited along with the ingredients it is desired to deposit, which can lead to dulling of the hair through excessive build up and reduced performance.

The prior art also proposes the use for suspending purposes of hydrophilic polymers which disperse in aqueous media. Natural polymers have been used for this purpose, and in particular xanthan gum has been used. Personal washing products, especially shampoos, containing xanthan gum are described for example in U.S. Pat. No. 5,286,405 and GB-A-2188060. A problem is that the resulting products often have an unacceptable "stringy" texture and a slimy feel.

One category of synthetic polymers used for suspending purposes are carboxyvinyl polymers. The carboxyvinyl polymers are colloidally water soluble polymers of acrylic acid cross-linked with polyallylsucrose or polyallylpentaerythritol, obtainable under the CARBOPOL trademark from B F Goodrich. U.S. Pat. No. 5,635,171 describes a transparent or translucid gel based on such polymers, in which the gel is rigidified by the incorporation of a very small quantity of an aqueous solution of galactomannan (carob, guar or tara gum). This rigidification enables the stabilization of suspended phases.

A problem is, however, that carboxyvinyl polymers of the above described type can be difficult to formulate because of, inter alia, their sensitivity to pH and ionic strength and their incompatibility with ethoxylated surfactants.

A number of polymers of biological origin, when in aqueous solution, have the ability to form so-called reversible gels, for example, those which melt when heated but revert to a gel when cooled down subsequently. One well known example of a polysaccharide which forms reversible gels is agar. An aqueous solution containing a small percentage of agar is a mobile liquid when hot, but when left to cool it forms a gel with sufficient rigidity to maintain its own shape. Other naturally derived polymers which can form reversible gels are carrageenan, furcelleran, gellan and pectin.

The formation of gels by natural polysaccharides arises from interaction between the polymer molecules. Reversible gels generally melt over a range of temperatures or display a melting temperature, referred to as the gel point. This is the temperature at which, on slow heating, the gel is observed to melt as this interaction largely disappears. Thus, above the gel point, the hot solution of polymer is mobile. When it cools below its gel point, the interaction of polymer molecules enables them to form a continuous and branched network which extends throughout the sample. In contrast with the formation of a continuous, branched network, some other materials which thicken water do so through merely local, transient entanglement of molecules. A discussion of polysaccharide gels, including their range of mechanical properties, is found in "Gels and Gelling" by Allan H Clark which is Chapter 5 in Physical Chemistry of Foods, Schwartzberg and Hartel, editors; published by Marcel Dekker 1992. In some instances, there is hysteresis and the melting and setting temperatures are not identical.

The melting temperature of a gel can suitably be measured by placing a steel ball, having a diameter of approximately 1 mm, on the surface of a sample which is fully set, then raising the temperature slowly, e.g., in a programmable water bath. The gel melting point is the temperature at which the ball begins to sink through the sample. Apparatus to facilitate such determinations is available, for example as a Physica AMV200 rolling ball viscometer from Anton Paar KG.

A reversible gel also displays a transition temperature at which, upon slow temperature increase, all ordering, be it of microscopical or macroscopical extent, has disappeared completely. This transition temperature (from order to disorder) can be measured by means of differential scanning calorimetry (DSC). The transition temperature of a reversible gel, as measured by DSC, usually approximately coincides with gel melting, observable visually.

EP-A-355908 teaches that polysaccharides which are capable of forming a reversible gel can be used to form viscous, yet mobile, fluid compositions by subjecting the composition to shear while gel formation takes place. The resulting compositions can be termed "shear gels".

Another way of forming a shear gel is to use a protein gel rather than a polysaccharide gel. An example of this is using a cold set whey gel as disclosed in U.S. Pat. No. 5,217,741, which is a gel created from pre-formed whey aggregates when the pH is changed or salt is added. This cold set whey gel can be produced as a shear gel of similar properties to that of the polysaccharide shear gels.

EP0250623 discloses the formation of whey particles by heating the whey solution under high shear to produce small heat set particles, that can be used as a fat replacement. The particles are not described as entrapping any material, nor are they described as a fluid gel with apparent yield stress properties.

We have now found that compositions comprising a continuous phase formed from such shear gels not only display excellent resistance to separation of components and settling of suspended materials but also can be used to entrap beneficial materials within the gel particles. "Entrap" is a used to describe situations where the beneficial materials are residing within a single gel particle and/or where the beneficial materials are associated with the gel matrix structure. The shear gels of these compositions are tolerant to the presence of many surfactants (eg, in personal wash or hair treatment compositions), and may under some circumstances enhance the delivery of the beneficial materials from the compositions.

WO98/08601 describes aqueous compositions such as liquid personal cleansers containing large hydrogel particles formed by two different water soluble polymers. The hydrogel particles trap water insoluble benefit agents in a network formed by these two polymers. The system is not a shear gel since it is prepared by first forming elongated polymer gel noodles which after gel formation are subsequently cut/broken into the desired gel particle size. The second polymer (which is typically an acrylic polymer such as CARBOPOL™ referred to above) is required to modify gel strength in order to help stabilise benefit agent in the polymer hydrogel system. WO95/12988 refers to suspensions or dispersions of gelled and hydrated biopolymer particles for use in food or personal care products to impart a fatty-like character to the product. This system is not a shear gel since particulation of dry material at a temperature equal to or above T(gel) is followed by hydration of the particles at a temperature lower than T(gel), the term "T(gel)" denoting the temperature at which, upon cooling, an aqueous solution of the biopolymer concerned, sets to a gel.

WO99/51193 discloses hair treatment compositions comprising a first (shear gel) phase and a second (suspended) phase. The second (suspended) phase is suspended in the shear gel phase ie, between the gel particles in any fluid that is present between the particles. Thus, in this document, the compositions are produced by forming the shear gel as a first step and then adding the material of the second (suspended) phase as a second step. It is clear that under these conditions the material of the second (suspended) phase may become associated with the exterior surface of the gel particles but that the gel particles will not substantially encapsulate the material of the second (suspended) phase.

WO99/26585 describes a washing composition containing an emulsion of silicone droplets. The silicone droplets contain a dispersed phase of solid particulate active agent, such as, for example, zinc pyridinethione (ZPTO). The silicone phase is a liquid phase, rather than a gel phase.

EP-A-0630580 teaches oil-coated gellan microparticles for use in foodstuffs as fat replacers. The microparticles may be used to encapsulate drugs, micro-organisms or enzymes. However, there is no disclosure in this document as to how such encapsulating microparticles may be formed, other than by way of extending a fluid gellable composition containing the material to be encapsulated through a hollow needle or fine orifice. The resulting product is not a shear gel.

WO98/11877 describes the formation of a dry powder produced by spray-drying gel-encapsulated liposomes. The product of the process is not discrete microencapsulated particles but a homogenous mass.

WO98/5000 relates to crushable gel beads formed of an agar complex as delivery vehicles for the topical delivery of biologically or cosmetically active agents.

EP-A-0590538 describes hair treatment compositions in which hair treatment compounds are encased in a shell material.

U.S. Pat. No. 5,089,269 teaches a cosmetic composition comprising micro-capsules enclosing a hydrophobic component. The micro-capsules are composed of a gelatin film swollen with water.

U.S. Pat. No. 5,641,480 discloses hair care compositions containing heteroatom-containing alkyl aldonamide compounds and hair conditioning agents.

The present invention provides shear gel compositions which comprise a phase that is entrapped in the gel particles.

The entrapment of active substances in the gel particles may cause the substances to have enhanced delivery to the site of action eg, controlled release and/or more selective delivery. Also, the entrapped phase has a reduced tendency to separate from the composition.

SUMMARY OF THE INVENTION

In a first aspect, the present invention provides a composition which has a thickened fluid form comprising:

(i) a first (shear gel) phase comprising at least one polymer which is capable of forming a gel, which polymer is present in the composition as a shear gel (i.e., a multiplicity of separate gel particles which have been formed by subjecting the polymer to shear while gel formation takes place); and (ii) a second (entrapped) phase which is in the form of particles or droplets comprising a hair benefit agent wherein at least some of the particles or droplets are entrapped in at least a proportion of the gel particles of the first (shear gel) phase.

In a second aspect, the invention provides a process for producing the composition of the invention which comprises forming an aqueous solution of the polymer, mixing the solution with particles or droplets of one or more hair benefit agents, which are substantially insoluble in the aqueous solution or substantially immiscible with the aqueous solution, and cooling the solution to a temperature below the gel formation temperature while applying shear to the composition.

In a third aspect, the invention provides the use of gel particles in a shear gel as a matrix for the controlled release and/or delivery of a substance which is entrapped in the matrix, in a hair treatment composition.

DETAILED DESCRIPTION AND PREFERRED EMBODIMENTS

First (Shear Gel) Phase

In the present specification, the expression "thickened fluid" is used to denote a composition with viscosity greater than that of water.

In order that the gel particles remain stable in the presence of surfactant (which will normally be present in hair treatment compositions of the invention), it will generally be desirable that the polymer does not require polyvalent cations in order to form the precursor molecular structures that are subsequently capable of intermolecular association leading to formation of a gel network. Consequently, it is desirable that the polymer is capable of forming a gel by another method, for example dissolving a sufficient concentration in hot distilled or demineralised water and allowing it to cool to a temperature low enough to permit gel formation (eg, an ambient temperature of about 20° C.). Other methods of gel formation include, for example, pH changes (eg, for the formation of cold set whey gels).

Polymers which are dependent on polyvalent cations for gelling (eg, alginate and gellan gum) can be employed to produce gel particles and used in hair treatment compositions, so long as they are stabilised against the surfactant (by employing e.g. a protective structure, such as amylose, around or within the gel). Alternatively, cross-linking agents can be used to stabilise proteins or polysaccharides against the disruptive effect of surfactants on gel structure.

Compositions embodying this invention may be made with viscosities in a wide range. At one extreme, the compositions may be freely mobile, self-levelling and pourable, although thicker than water. On the other hand, they may be made as viscous liquids which can be squeezed from a collapsible container, and yet which are too viscous to pour, except very slowly.

They are shear-thinning, which can be a useful property in hair treatment compositions such as shampoos and conditioners, because the user can perceive the product as thick and viscous, and yet find it easy to apply. An advantage of viscous shear gels is that they are good at retaining the shape which has been squeezed out, and so can be dispensed by methods other than simple pouring such as from flexible or deformable squeeze tubes.

If the compositions are heated to a temperature above the melting temperatures, the individual gel particles will melt and will not reform as separate particles on cooling quiescently, but this will not be a problem in ordinary use, because reversible gels generally have melting temperatures well above normal room temperatures (eg, 20° C.). (Irreversible gels are temperature stable by definition and include whey gels.)

Viscosity of compositions embodying this invention can be measured using the same techniques as are used to measure viscosities of other thickened liquid compositions. One suitable apparatus is the Haake Rotoviscometer™, another is the Carri-Med CSL 500™ viscometer.

Many compositions of this invention will display a viscosity in a range from 0.1 Pa.s to 1000 Pa.s at a shear rate of 10 sec-1 measured at 20° C.

Typically, the gel particles in the shear gel phase will have an average size (ie, maximum dimension) in the range of from 1 $\mu$m to 1000 $\mu$m, more preferably 5 $\mu$m to 100 $\mu$m and most preferably 10 to 80 $\mu$m, although particles having sizes falling outside this range may also be present in the shear gel phase.

One route for the preparation of the sheared gel particles required for this invention, according to the process of the invention, starts with the provision of an aqueous solution of the polymer, at a temperature above the gel melting temperature (and probably also above its order to disorder transition temperature), mixing the solution with particles or droplets of one or more hair benefit agents, which are substantially insoluble in, or immiscible with, the aqueous solution, then cooling the solution to a temperature below the gel setting temperature, while applying shear to the composition. Generally, the solution will be subjected to shear while cooling from, for example, 10° C. higher than the gel melt temperature to, for example, 10° C. to 20° C. lower than the gel formation temperature.

On a small scale, this preparation may be carried out using a beaker and a mechanical stirrer to provide vigorous stirring while the contents of the beaker are allowed to cool.

We prefer to carry out the preparation using a scraped surface heat exchanger. This may be equipped to operate under a partial vacuum to reduce the incorporation of air bubbles into the composition as gel formation takes place.

Another possibility for preparing gel particles is to employ a "Stirred Pot" where the solution is quench cooled in a jacketed shear device fitted with a thermometer.

Alternatively, the shear gel may be formed by providing cooling by means of passing the solution and additives through a plate heat exchanger. Plate heat exchangers are well known units marketed by companies such as Alfa Laval and APV. In this device, the solution is transformed into a shear gel as it passes through channels of the plate heat exchanger. Shear is transmitted to the solution due to the flow through the channels, rather than by a rotor as in methods described previously in this application. The production of shear gels using the plate heat exchanger may take place in re-circulation mode or in single pass mode. In re-circulation mode the solution is pumped from the base of a stirred batch vessel into the plate heat exchanger and then back into the stirred tank. This operation terminates when the temperature of the entire batch has reached the desired value, below the gelation point of the polymer solution. In single pass mode, the solution will reach the desired temperature upon exiting from the heat exchanger. The plate heat exchanger may be operated in co-current or counter-current mode with respect to the flow direction of the cooling medium. Through installation of suitable diverters the exchanger may be operated in single pass or multipass configuration, depending on heat transfer performance required in the particular application.

Furthermore, the plate heat exchanger may be operated in series with an in-line dynamic mixing device, such as a Silverson or Dispax mixer. This device provides the ability to break down the shear gel particles formed in the stirred vessel, scraped surface heat exchanger or plate heat exchanger. Thus the in line dynamic mixer provides some control over gel particle size.

We have found that for many polymers gel formation is inhibited by the presence of surfactant (which is normally a component of hair treatment compositions), and yet gel particles which have already been formed remain stable if surfactant is added subsequently.

Therefore, if the final composition is to contain a surfactant, generally it will be desirable to form the gel particles by cooling an aqueous solution of the gel-forming polymer in the substantial absence of surfactant, and then add surfactant subsequently. An alternative approach is to incorporate surfactant into the aqueous composition before the step of cooling under shear, but this is not possible for all gel-forming polymers.

Thus, the process of the invention may involve a method of preparing a composition comprising a surfactant (such as in a personal wash or hair treatment composition) as set forth above which comprises forming a hot (eg, 40° C. to 100° C.), mobile aqueous solution of the polymer, mixing the solution with particles or droplets of one or more substances which are substantially insoluble in, or immiscible with, the aqueous solution, cooling the solution through its gel temperature, subjecting it to shear during or after cooling, and incorporating surfactant possibly before but preferably after cooling through the gel temperature.

A laboratory-scale scraped surface heat exchanger which we have used successfully is the ESCO Labor™ mixer available from ESCO Labor, CH-4125, Reihen, Germany.

Scraped surface heat exchangers (A-units) homogenisers and temperature controlled pin-mixers (C-units) are used in the commercial production of margarine and other spreadable foodstuffs and such apparatus may be used to produce compositions of this invention on a larger scale. A discussion of such heat exchangers is given by Harrod in Journal of Food Process Engineering 9 (1986) pages 1–62. Suppliers of such apparatus include Armfield Ltd, Ringwood, Hampshire, England, Contherm Corporation which is a division of the Alfa-Laval Group, USA and APV Projects (Crepaco) Ltd, Crawley, West Sussex, England.

An alternative jacketed shear device that has been used successfully to make the shear gels of the invention is the stirred pot (illustrated in FIG. 1b) which is cooled using a Tricool chiller system supplied by Tricool Engineering Limited, Solent House, 14 Barnes Wallis Road, Segensworth East, Fareham, Hampshire, PO5 5TT.

After the formation of gel particles, the addition of surfactant or other ingredients, probably as a liquid concentrate, can be carried out using conventional mixing apparatus, operating at low shear. A mixing operation should not be allowed to heat the composition sufficiently to cause the melting of the gel particles. If necessary, a composition containing gel particles should be cooled before and/or during any subsequent mixing operation.

One route for producing a protein shear gel is illustrated, for example, by the process of cold set whey gelation. Cold set gels are produced by a two step process, the first involves heating the protein under conditions where it does not gel but produces soluble nm size linear protein aggregates. This usually means at high or low pH and in the absence of salt. The aggregates are prevented from aggregating by electrostatic repulsion. These aggregates are then induced to gel by changing the solution conditions to remove this repulsion. This is either achieved by adding salt to screen the charge or changing the pH.

In order to produce a whey shear gel, this two step process is also carried out but the second gelation step is carried out under shear. This shear could be produced in a variety of methods as described earlier for example a 'stirred pot' or a scraped surface heat exchanger. In order to entrap an ingredient within the whey particles, it may be added to the whey solution before the initial heating step, or after the heating step and before the gelation under shear. This addition is achieved by mixing the solution with particles or droplets of one or more substances which are substantially insoluble in, or immiscible with, the aqueous solution. The gelation is induced usually by a change in pH, for example, to take the solution from pH 7 to between pH 3.5 and 6. Preferably, this change can be achieved, by adding acid directly to the whey while it is under shear, or by adding a slow acidifier for example GDL (glucono-δ-lactone) which will change the pH slowly while the sample is sheared.

Materials and procedures useful in this invention will now be described in greater detail, making reference to the accompanying drawings wherein:

FIG. 1a is a cross-section of a laboratory mixer useful for preparing shear gel particles on a batch basis, FIG. 1b shows a cross-section of an alternative mixer useful for preparing shear gel particles on a batch basis.

FIG. 2 diagrammatically illustrates apparatus for continuous preparation;

FIG. 3 shows zinc pyridinethione (ZnPTO) particles entrapped within sheared agar gel particles;

FIG. 4 illustrates levels of ZnPTO deposition for a hair treatment composition of the invention compared to compositions of the prior art and compositions where the ZnPTO is not actually entrapped within the different sheared gels, but is free amongst the agar sheared gel particles; and FIGS. 5 and 6 are low and high magnification images, respectively, of sheared agar gel particles containing silicone oil droplets.

Figure 1A:
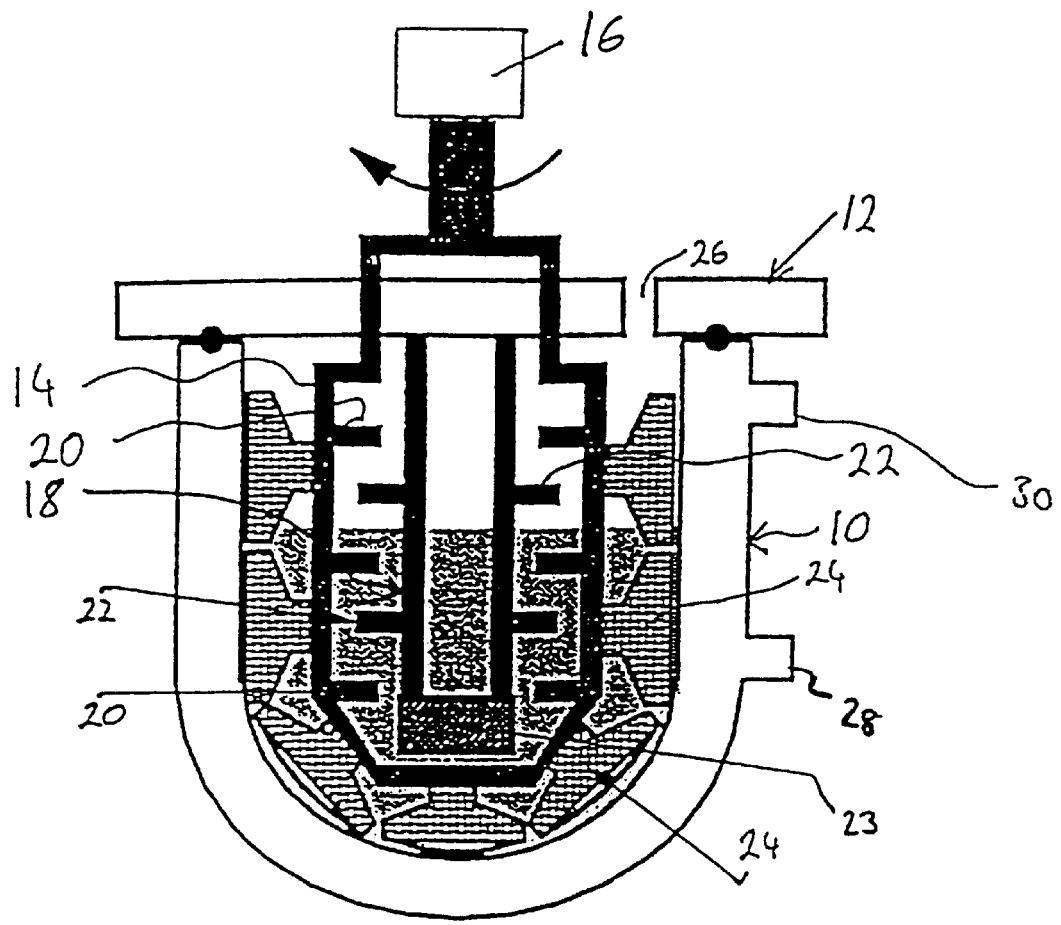

The apparatus shown in FIG. 1a may be a TK AEI homo mixer. It has a containing vessel 10 with inner and outer walls spaced apart to allow a coolant to be circulated through the space between them. The vessel has an upper closure 12. Rotor 14 within the vessel is extended through the upper closure 12 and connected to a drive motor 16. The rotor 14 surrounds a central fixed stator 18. Baffles 20, 22 project from the rotor 14 and stator 18 respectively. Homogeniser 23 is situated at one end of stator 18. When rotor 14 is turned, the liquid within vessel 10 is subjected to shear by the movement of rotor 14 and its baffles 20 relative to stator 18 and its baffles 22. In addition flaps 24 (preferably made of polytetrafluoroethylene) projecting from rotor 14 scrape the inner wall of vessel 10. The upper closure 12 includes provision at 26 for connection to a vacuum pump. Gas tight seals are provided between the rotor 14 and the upper closure 12. Consequently vacuum can be applied to the interior of the vessel 10 through the connection 26. Water flows in at inlet 28 and out from outlet 30.

In order to make a composition according the invention using this apparatus an aqueous solution of the polymer, heated to above its gel temperature, and containing particles or droplets of the material forming the second (entrapped) phase of the composition uniformly mixed with the solution, is placed in the vessel. The upper closure 12 is then placed on the vessel and the contents of the vessel are cooled by circulation of coolant via inlet 28 and outlet 30 through the space between the vessel walls. At the same time the rotor is turned and vacuum is applied to the connection 26 so that cooling of the vessel contents takes place under conditions of shear, while suction through the air outlet 26 prevents formation of gas bubbles.

In consequence, as the contents of the vessel cool to below the gel point, a multiplicity of small gel particles are formed. Once the contents of the vessel have cooled below the gel temperature and these particles have formed, surfactant can be mixed with the vessel contents either by removing the upper closure and adding a liquid concentrate of the surfactant to the vessel 10, or by transferring the contents of the vessel 10 and also the surfactant, to a separate mixer.

Figure 1B:
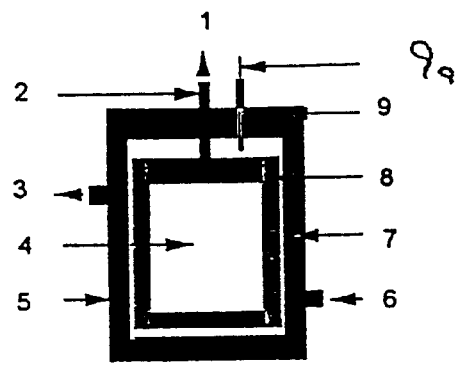

FIG. 1b shows a stirred pot which can be used in an alternative method by which shear gels may be produced. It has a containing cell 5 (eg, of glass) (for example 300 ml volume) which is surrounded by a temperature jacket 7 through which water flows from 6 to 3. A paddle stirrer 2 within the vessel is extended through the sealed lid 9 and connected to a drive motor 1. Baffles 8 (eg, of or coated with TEFLON™) extend from the paddle stirrer. A temperature probe 9a measures the temperature of the mixture 4.

Figure 2:
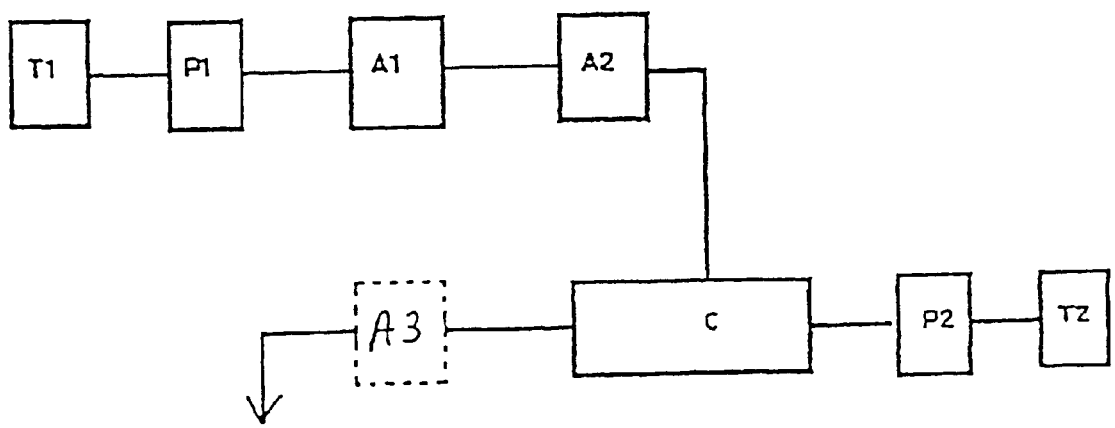

FIG. 2 illustrates a preferred form of apparatus consisting of several individual pieces of equipment connected together by pipework.

A hot aqueous solution of the polymer is prepared and held in a supply vessel T1. It is delivered from this by a suitable pump P1 to a scraped surface heat exchanger A1 which is in the form of a cylinder through which the polymer solution flows and which is surrounded by a jacket for coolant. Within this heat exchanger is located a large diameter shaft fitted with scraper blades which are spring loaded to hold them against the interior surface of the cylindrical vessel wall. Rotation of this central shaft by a motor applies shear to the polymer solution as it passes through the heat exchanger A1.

As the polymer solution passes through the heat exchanger A1 it is cooled to below its gel temperature under conditions of shear and this leads to the formation of gel particles in a continuous aqueous phase. The resulting composition passes on from heat exchanger A1 to a second heat exchanger A2 which is similar except that it operates at a lower speed. This is used to cool the composition further.

The composition then flows on to a mixer C which, like the units A1 and A2 performs a heat exchange function. However, within this C-unit there are stationary baffles projecting inwardly from the heat exchanger walls and a motor driven central, small diameter shaft which carries further baffles that project between the stationary baffles of the cylinder wall. There are no scrapers in this device. Here the composition is mixed with surfactant solution delivered from a supply vessel T2 by means of a suitable pump P2. The mixture leaving the high speed mixer C is a composition in accordance with the present invention. It may be convenient to cool it by passage through a further scraped surface heat exchanger A3 operating at low speed before the composition is delivered as finished product or packed in containers.

The pumps P1 and P2 may conveniently be provided as separate channels of a proportioning piston pump, which is a convenient way to ensure that constant proportions are delivered from each of the tanks T1, T2.

Mixing apparatus, pumps and scraped surface heat exchangers used in apparatus as above can be of types which are customarily used in the production of margarine and other edible spreads. Another name for the combination of scraped surface heat exchangers and mixing devices which provides for through flow of the material is a "votator". These pieces of apparatus may be manufactured in a range of sizes extending from small units which can fit on a laboratory bench to full scale production plant. Manufacturers of such apparatus include Armfield Ltd., Contherm Corporation and APV Projects (Crepaco) Ltd mentioned above.

Other plant designs capable of meeting the essential requirement of cooling polymer solutions through their gelation process whilst applying substantial shear forces to all the fluid can also be envisaged and fall within the scope of the process of this invention.

Polymer Types

Compositions of this invention contain a polymer capable of forming a gel. It is desirable that the polymer should be capable of forming a gel without requiring metal salt to be present. (Polymers which require ionic species to be present as a prerequisite for gel formation are apt to be destabilised by surfactant, even if formed as shear gel particles). Generally, this means that such a polymer, dissolved in demineralised water at some concentration between 0.04 and 10% by weight will form a gel on cooling the solution without agitation from an elevated temperature of for example, around dissolving temperature to 10–20° C. lower than the gel formation temperature (eg, 20° C. to 90° C. for 24 hours).

In this test of gel-formation, a polymer may or may not form a gel at every concentration in the range from 0.04% to 10% by weight. With some polymers, concentrations as high as 10% by weight may not be achievable. Some polymers may form gels without standing for as long as 24 hours.

The polymer is preferably selected from the group consisting of polysaccharides, proteins and mixtures thereof. More preferably the polymer is selected from carrageenan, furcellaran, pectin, alginate, agar, gellan, glucomannans (e.g. Konjac), galactomannans (e.g. locust bean gum, guar), xanthan, modified celluloses, glucans (e.g. starches, curdlan), gelatin, whey protein and mixtures thereof; most preferably agar, carrageenan or whey protein.

The polymer which is capable of forming a gel will usually be one or more polysaccharides (eg, naturally derived).

One polysaccharide which may be used is agar, which is of course well known for use as a growth medium for microorganisms in vitro.

Agarose is a linear polysaccharide, basically made up from β-1,3 galactose residues alternating with α-1,4 galactose residues. The latter are present as the 3,6 anhydride and are the L-enantiomer.

Agaropectin likewise has β-1,3 galactose residues alternating with α-1,4 galactose residues, but includes sulphate, pyruvate and/or glucuronic acid residues.

The term agar covers a family of polymers containing agarose and/or agaropectin, i.e., polymers with backbone structure containing alternating 1,3-D-galactose and 1,4-L-galactose residues.

Agar is extracted from certain species of red seaweed, principally in Japan. A description of agar is given by Tetsujiro Matsuhashi as Chapter 1 in "Food Gels" edited by Peter Harris, Elsevier, 1990.

Another category of polysaccharide which may be used is the kappa carrageenans. Carrageenans are a class of polysaccharides which occur in some other red seaweed species. They are linear polysaccharides made up from alternating β-1,3- and α-1,4-linked galactose residues. The 1,4-linked residues are the D-enantiomer and sometimes occur as the 3,6-anhydride. Many of the galactose residues are sulphated.

A number of carrageenan structures have been described and commercial materials are available which approximate to the ideal structures. However, variations between these structures occur, depending on the source of the carrageenan and treatment of it after extraction.

A description of different carrageenan types is given in "Carrageenans" by Norman F Stanley which is Chapter 3 of "Food Gels" mentioned above.

Kappa carrageenan is sulphated on the 1,3-linked galactose residues, but not on the 1,4-linked residues. Iota carrageenan is sulphated on both residues. Lambda carrageenan has two sulphate groups on the 1,4-linked residues and one sulphate group on 70% of the 1,3-linked residues.

Other types of carrageenan may be used in mixtures with kappa. Aqueous solutions of iota carrageenan exist as reversible gels, but these appear to be self-healing. Iota carrageenan can be used to form compositions in accordance with this invention, but the compositions become lumpy during storage because of the self-healing property of iota carrageenan gels, and so for this invention it is desirable to use kappa carrageenan or mixtures of kappa and iota.

Lambda carrageenan on its own in aqueous solution does not form gels because its higher charge density inhibits association between molecules and consequent structuring in liquids. However, some lambda carrageenan may be included in mixtures with kappa, or may be present as an impurity in commercial supplies of kappa or iota carrageenan.

If lambda carrageenan is included in a mixture of carrageenans, the mixture may contain a majority (more than one half of the polysaccharide) of kappa or kappa and iota carrageenan with a minority proportion of lambda carrageenan.

Another polymer which may be used is furcellaran. Furcellaran is similar to kappa carrageenan, but is only partially sulphated on the 1,3-linked galactose residues.

A polymer of bacterial origin which may be used is gellan. It is the polymer of a tetrasaccharide repeat unit, containing glucose, glucuronic acid, and rhamnose residues. There is some substitution with acyl groups but these are often removed during production to give a low acyl gellan. Gellans are the subject of Chapter 6 by G R Saunderson in "Food Gels" mentioned above.

Another possibility is to use a so-called synergistic gel which relies on the interaction of two polymer types. In general these may be formed from a polysaccharide which is a glucomannan with sequences of mannose residues in its polymer chain, such as locust bean gum or guar gum, and a second polymer which is xanthan or carrageenan.

A further possibility is to use starch, especially amylose, in mixtures with polymers that are dependent on a metal salt for their gelation.

Other polymers include proteins, such as, for example, gelatin or whey protein gels.

It is possible to include an additional thickening agent, such as a small concentration of xanthan gum, curdlan, modified starches or celluloses in the composition in addition to the gel particles. This may possibly be added after gel particles have been formed along with surfactant.

Polymers capable of forming a gel may constitute from 0.04 to 10 wt % of the whole composition, often from 0.1 to 5 wt %.

In general, the viscosity of a shear gel composition in accordance with this invention will increase with the concentration of polymer contained in it.

Viscosity will also be affected by the size and shape of the gel particles, which in turn is affected by the conditions used to apply shear during cooling. In general, combinations of variable cooling rates and different rotor speeds during shearing permits the optimisation of particle dispersion smoothness, suspending properties and viscosity, possibly because gel particle shapes can vary between spherical and filamentous forms.

Non-Surfactant Electrolyte

Although it is generally desirable that the polymer should be capable of forming a gel without participation of ionic species, some polymers which are capable of forming a gel in distilled or demineralised water, nevertheless, form gels of greater viscosity if some electrolyte is present. Notably the viscosity of Kappa carrageenan gel dispersions is increased by the presence of potassium ions and the viscosity of agar gel dispersions is increased in the presence of calcium ions. Consequently, a polymer solution which is cooled under shear to form gel particles as required for this invention may include electrolyte to enhance the strength of the resulting gel particles. The amount of electrolyte required may be a small percentage of the product, e.g. 1%.

Second (Entrapped) Phase

The entrapped phase in the compositions of the invention may comprise any hair benefit agent which it is usually desired to incorporate in the compositions. Preferably, the material of the entrapped phase requires some degree of stabilization in the composition against phase separation and settling under normal storage conditions, or benefits from segregation away from other formulation components, or benefits from enhanced delivery when entrapped.

The entrapped phase is in the form of particles of insoluble solids or droplets of immiscible liquids, at least some of which are entrapped within the gel particles. Preferably, at least 50% by weight, more preferably at least 75% by weight, most preferably at least 95% by weight, of the insoluble solids or immiscible liquids in the composition are entrapped in the gel particles. The gel particles may contain on average one particle or droplet of the encapsulated phase or, preferably, a plurality of particles or droplets. Particles or droplets may also be associated with the outer surface of the gel particles, although it is essential that at least a proportion of them reside within the gel particles.

The particles or droplets of the entrapped phase preferably have an average size (ie, their maximum dimension) in the range of from 0.002 µm to 50 µm, preferably from about 0.01 µm to 10 µm, although it is essential that the particles or droplets are smaller in size than the gel particles of the shear gel phase.

The entrapped phase is substantially insoluble in (in the case of solid particles) or immiscible with (in the case of liquid droplets) the entrapping gel phase and the aqueous solution from which they are formed. Therefore, the entrapped phase will typically have a solubility in water of less than about 0.05 g/l (preferably less than about 0.01 g/l) at 20° C.

The identity of the entrapped phase will depend upon the nature of the particular composition. However, the entrapped phase consists of or comprises a hair benefit agent. The term hair benefit agent includes materials which can provide a benefit to the hair and/or the scalp and/or the skin (preferably the hair and/or the scalp) as well as those materials which are beneficially incorporated into hair treatment products (eg, aesthetic agents). Hair benefit agents include conditioning agents and solid active agents as defined hereinafter.

Third (Suspended) Phase

The first (shear gel) phase may comprise a third (suspended) phase suspended therein, as described in WO99/51193. The third (suspended) phase may be selected from the same materials described hereinafter for the second (entrapped) phase and, in any particular composition, may be the same as, or different from, the material of the second (entrapped) phase.

Product Compositions

Personal Care Compositions

In one product form, the composition may be a personal washing composition. Typically, the personal washing composition will contain one or more surfactants. The entrapped phase in personal washing compositions of the invention may comprise one or more of the conditioning agents, aesthetic agents and solid active agents described hereinafter in relation to hair treatment compositions of the invention. Alternatively, other solid and/or liquid active materials which are beneficially applied to the skin may be incorporated into the personal washing compositions of the invention.

Hair Treatment Compositions

Preferably, the compositions of the invention are hair treatment compositions and the entrapped phase and, when present, the third suspended phase, is a hair benefit agent selected from one or more of the following classes of material:

Conditioning Agents

As used herein, the term "conditioning agent" includes any material which is used to give a particular conditioning benefit to hair and/or skin. For example, in compositions for use in washing hair, such as shampoos and conditioners, suitable materials are those which deliver one or more benefits relating to shine, softness, combability, wet-handling, anti-static properties, protection against damage, body, volume, stylability and manageability.

Preferred conditioning agents for use in the present invention include emulsified silicones, used to impart for example wet and dry conditioning benefits to hair such as softness, smooth feel and ease of combability.

Various methods of making emulsions of particles of silicones for use in the invention are available and are well known and documented in the art.

The viscosity of the silicone itself (not the emulsion or the final washing composition) preferably ranges from 10,000 cps to 5 million cps. The viscosity can be measured by means of a glass capillary viscometer as set out further in Dow Corning Corporate Test Method CTM004 Jul. 20, 1970.

Suitable silicones include polydiorganosiloxanes, in particular polydimethylsiloxanes which have the Cosmetics &

Toiletries formulatory Association (CTFA) designation dimethicone. An example is dimethicone fluid having a viscosity of up to 100,000 centistokes at 25° C., which is available commercially from the General Electric Company as the Viscasil™ series and from Dow Corning as the DC 200™ series.

Aminofunctional silicones which have the CTFA designation amodimethicone, are also suitable for use in the compositions of the invention, as are polydimethyl siloxanes having hydroxyl end groups, which have the CTFA designation dimethiconol.

Also suitable are silicone gums. "Silicone gum" denotes polydiorganosiloxanes having a molecular weight of from 200,000 to 1,000,000 and specific examples include dimethicone gums, dimethiconol gums, polydimethyl siloxane/diphenyl/methylvinylsiloxane copolymers, polydimethylsiloxane/methylvinylsiloxane copolymers and mixtures thereof. Examples include those materials described in U.S. Pat. No. 4,152,416 (Spitzer), and on General Electric Silicone Rubber product Data Sheet SE 30, SE 33, SE 54 and SE 76.

Also suitable for use in the present invention are silicone gums having a slight degree of cross-linkcing, as are described for example in WO96/31188. These materials can impart body, volume and stylability to hair, as well as good wet and dry conditioning.

Preferred emulsified silicones for use in compositions of the invention have an average silicone particle size in the composition of less than 100, preferably less than 30, more preferably less than 20 microns, most preferably less than 10 microns.

Particle size may be measured by means of a laser light scattering technique, using a 2600D Particle Sizer from Malvern Instruments.

Suitable silicone emulsions for use in the invention are commercially available in a pre-emulsified form. This is particularly preferred since the pre-formed emulsion can be incorporated into the washing composition by simple mixing.

Examples of suitable pre-formed emulsions include emulsions DC2-1766 and DC2-1784, available from Dow Corning. These are emulsions of dimethiconol. Cross-linked silicone gums are also available in a pre-emulsified form, which is advantageous far ease of formulation. A preferred example is the material available from Dow Corning as DC X2-1787, which is an emulsion of cross-linked dimethiconol gum.

The amount of silicone incorporated into the compositions of the invention depends on the level of conditioning desired and the material used. A preferred amount is from 0.01 to about 10% by weight of the total composition although these limits are not absolute. The lower limit is determined by the minimum level to achieve conditioning and the upper limit by the maximum level to avoid making the hair and/or skin unacceptably greasy. We have found that an amount of silicone of from 0.5 to 1.5% by weight of the total composition, is a particularly suitable level.

A further preferred class of conditioning agents are per-alk(en)yl hydrocarbon materials, used to enhance the body, volume and stylability of hair.

EP 567 326 and EP 498 119 describe suitable peralk(en)yl hydrocarbon materials for imparting stylability and enhanced body to hair. Preferred materials are polyisobutylene materials available from Presperse, Inc. under the PERMETHYL trade name.

The amount of per-alk(en)yl hydrocarbon material incorporated into the compositions of the invention depends on the level of body and volume enhancement desired and the specific material used. A preferred amount is from 0.01 to about 10% by weight of the total composition although these limits are not absolute. The lower limit is determined by the minimum level to achieve the body and volume enhancing effect and the upper limit by the maximum level to avoid making the hair unacceptably stiff. We have found that an amount of per-alk(en)yl hydrocarbon material of from 0.5 to 2% by weight of the total composition is a particularly suitable level.

Solid Active Agents

Examples of typical solid-active agents include antimicrobials such as the heavy metal salts of pyridinethione (also known in the art as "pyrithione"), especially zinc pyridinethione, and other antimicrobials such as climbazole, sulphur, piroctone olamine, octopirox, selenium disulphide and ketoconazole. These substances typically have an average particle diameter of from about 0.2 to about 50 microns, preferably from about 0.4 to about 10 microns. These solid active agents are the preferred material for the entrapped phase. Although the materials may have effect on the skin and/or the scalp, they are understood by those skilled in the art to be useful in hair treatment compositions for treating dandruff (eg, antidandruff shampoos) and are encompassed within the term "hair benefit agent", as used herein.

Where the solid active agent is an antimicrobial agent, such as zinc pyridinethione, this may be suitably be employed in the composition in an amount of from 0.001% to about 1% by weight of the total composition.

Other suitable solid active agents include pigment particles, such as solid dyes or colorants suitable for application to hair, and metal colloids.

Aesthetic Agents

Hair treatment compositions such as shampoos and conditioners, and some personal washing compositions, are frequently opacified or pearlised to enhance consumer appeal.

Examples of opacifying agents include higher fatty alcohols (e.g. cetyl, stearyl, arachidyl and behenyl), solid esters (e.g. cetyl palmitate, glycerol laurate, stearamide MEA-stearate), high molecular weight fatty amides and alkanolamides and various fatty acid derivatives such as propylene glycol and polyethylene glycol esters. Inorganic materials used to opacify hair treatment compositions include magnesium aluminium silicate, zinc oxide, and titanium dioxide.

Pearlescing agents typically form thin, platelet-type crystals in the composition, which act like tiny mirrors. This gives the pearl lustre effect. Some of the opacifying agents listed above may also crystallise as pearlescing agents, depending on the media in which they are used and the conditions employed.

Typical pearlescing agents may be selected from C16–C22 fatty acids (e.g. stearic acid, myristic acid, oleic acid and behenic acid), esters of C16–C22 fatty acid with alcohols and esters of C16–C22 fatty acid incorporating such elements as alkylene glycol units. Suitable alkylene glycol units may include ethylene glycol and propylene glycol. However, higher alkylene chain length glycols may be employed. Suitable higher alkylene chain length glycols include polyethylene glycol and polypropylene glycol.

Examples are polyethylene glycol mono or diesters of C16–C22 fatty acids having from 1 to 7 ethylene oxide units, and ethylene glycol esters of C16–C22 fatty acids. Preferred esters include polyethylene glycol distearates and ethylene glycol distearates. Examples of a polyethylene glycol distearate available commercially are EUPERLAN PK900 (ex Henkel) or GENAPOL TS (ex Hoechst). An example of an ethylene glycol distearate is EUPERLAN PK3000 (ex Henkel).

Other pearlescing agents include alkanolamides of fatty acids having from 16 to 22 carbon atoms, (e.g. stearic monoethanolamide, stearic diethanolamide, stearic monoisopropanolamide and stearic monoethanolamide stearate); long chain esters of long chain fatty acids (e.g. stearyl stearate, cetyl palmitate); glyceryl esters (e.g. glyceryl distearate), long chain esters of long chain alkanolamides (e.g. stearamide DEA distearate, stearamide MEA stearate), and alkyl (C18–C22) dimethyl amine oxides (e.g. stearyl dimethyl amine oxide).

Further suitable pearlescing agents include inorganic materials such as nacreous pigments based on the natural mineral mica. An example is titanium dioxide coated mica. Particles of this material may vary in size from 2 to 150 microns in diameter. In general, smaller particles give rise to a pearly appearance, whereas particles having a larger average diameter will result in a glittery composition.

Suitable titanium dioxide coated mica particles are those sold under the trade names TIMIRON (merck) or FLAMENCO (Mearl).

The level of opacifying or pearlescing agent employed in compositions of the invention is generally from 0.01 to 20%, preferably 0.01 to 5%, more preferably from 0.02 to 2% by weight of the total composition.

Gas (e.g. air) bubbles represent another type of suspended phase that may be introduced into a hair treatment composition for aesthetic purposes. When evenly sized and homogeneously dispersed in the composition, these can enhance consumer appeal—a typical application is in a transparent or translucent composition such as a hair styling gel.

Product Form

Hair treatment compositions of the present invention may be formulated as transparent or opaque emulsions, lotions, creams, pastes, or gels. Particularly preferred product forms are shampoos, conditioners and hair styling gels.

Shampoo Compositions

A particularly preferred hair treatment composition in accordance with the invention is a shampoo composition. Such a shampoo composition will comprise one or more cleansing surfactants which are cosmetically acceptable and suitable for topical application to the hair. Further surfactants may be present as an additional ingredient if sufficient for cleansing purposes is not provided as emulsifier for any emulsified components in the composition, e.g. emulsified silicones. It is preferred that shampoo compositions of the invention comprise at least one further surfactant (in addition to that used as emulsifying agent) to provide a cleansing benefit.

Suitable cleansing surfactants, which may be used singularly or in combination, are selected from anionic, amphoteric and zwitterionic surfactants, and mixtures thereof. The cleansing surfactant may be the same surfactant as the emulsifier, or may be different.

Examples of anionic surfactants are the alkyl sulphates, alkyl ether sulphates, alkaryl sulphonates, alkanoyl isethionates, alkyl succinates, alkyl sulphosuccinates, N-alkyl sarcosinates, alkyl phosphates, alkyl ether phosphates, alkyl ether carboxylates, and alpha-olefin sulphonates, especially their sodium, magnesium, ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from 1 to 10 ethylene oxide or propylene oxide units per molecule.

Typical anionic surfactants for use in shampoos of the invention include sodium oleyl succinate, ammonium lauryl sulphosuccinate, ammonium lauryl sulphate, sodium dodecylbenzene sulphonate, triethanolamine dodecylbenzene sulphonate, sodium cocoyl isethionate, sodium lauryl isethionate and sodium N-lauryl sarcosinate. The most preferred anionic surfactants are sodium lauryl sulphate, triethanolamine monolauryl phosphate, sodium lauryl ether sulphate 1 EO, 2EO and 3EO, ammonium lauryl sulphate and ammonium lauryl ether sulphate 1EO, 2EO and 3EO.

Examples of amphoteric and zwitterionic surfactants include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates, alkyl amidopropyl hydroxysultaines, acyl taurates and acyl glutamates, wherein the alkyl and acyl groups have from 8 to 19 carbon atoms. Typical amphoteric and zwitterionic surfactants for use in shampoos of the invention include lauryl amine oxide, cocodimethyl sulphopropyl betaine and preferably lauryl betaine, cocamidopropyl betaine and sodium cocamphopropionate.

The shampoo composition can also include co-surfactants, to help impart aesthetic, physical or cleansing properties to the composition. A preferred example is a nonionic surfactant, which can be included in an amount ranging from 0% to about 5% by weight of the total composition.

For example, representative nonionic surfactants that can be included in shampoo compositions of the invention include condensation products of aliphatic (C8–C18) primary or secondary linear or branched chain alcohols or phenols with alkylene oxides, usually ethylene oxide and generally having from 6 to 30 ethylene oxide groups.

Other representative nonionics include mono- or di-alkyl alkanolamides. Examples include coco mono- or di-ethanolamide and coco mono-isopropanolamide.

Further nonionic surfactants which can be included in shampoo compositions of the invention are the alkyl polyglycosides (APGs). Typically, the APG is one which comprises an alkyl group connected (optionally via a bridging group) to a block of one or more glycosyl groups. Preferred APGs are defined by the following formula:

RO—(G)n wherein R is a branched or straight chain alkyl group which may be saturated or unsaturated and G is a saccharide group.

R may represent a mean alkyl chain length of from about C5 to about C20. Preferably R represents a mean alkyl chain length of from about C8 to about C12. Most preferably the value of R lies between about 9.5 and about 10.5. G may be selected from C5 or C6 monosaccharide residues, and is preferably a glucoside. G may be selected from the group comprising glucose, xylose, lactose, fructose, mannose and derivatives thereof. Preferably G is glucose.

The degree of polymerisation, n, may have a value of from about 1 to about 10 or more. Preferably, the value of n lies in the range of from about 1.1 to about 2. Most preferably the value of n lies in the range of from about 1.3 to about 1.5.

Suitable alkyl polyglycosides for use in the invention are commercially available and include for example those materials identified as: Oramix NS10TM ex SeppicTM; Plantaren 1200TM and Plantaren 2000TM ex Henkel.

The total amount of surfactant (including any co-surfactant, and/or any emulsifier) in shampoo compositions of the invention is generally from 0.1 to 50% by weight, preferably from 5 to 30%, more preferably from 10% to 25% by weight of the total shampoo composition.

A cationic deposition polymer is a preferred ingredient in shampoo compositions of the invention, for enhancing conditioning performance of the shampoo. By "deposition polymer" is meant an agent which enhances deposition of the silicone component from the shampoo composition onto the intended site during use, i.e. the hair and/or the scalp.

The deposition polymer may be a homopolymer or be formed from two or more types of monomers. The molecular weight of the polymer will generally be between 5 000 and 10 000 000, typically at least 10 000 and preferably in the range 100 000 to about 2 000 000. The polymers will have cationic nitrogen containing groups such as quaternary ammonium or protonated amino groups, or a mixture thereof.

The cationic nitrogen-containing group will generally be present as a substituent on a fraction of the total monomer units of the deposition polymer. Thus, when the polymer is not a homopolymer it can contain spacer non-cationic monomer units. Such polymers are described in the CTFA Cosmetic Ingredient Directory, 3rd edition. The ratio of the cationic to non-cationic monomer units is selected to give a polymer having a cationic charge density in the required range.

Suitable cationic deposition polymers include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have C1–C7 alkyl groups, more preferably C1–3 alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition. In general secondary and tertiary amines, especially tertiary, are preferred.

Amine substituted vinyl monomers and amines can be polymerized in the amine form and then converted to ammonium by quaternization.

The cationic deposition polymers can comprise mixtures of monomer units derived from amine- and/or quaternary ammonium-substituted monomer and/or compatible spacer monomers.

Suitable cationic deposition polymers include, for example:

copolymers of 1-vinyl-2-pyrrolidine and 1-vinyl-3-methylimidazolium salt (e.g. chloride salt), referred to in the industry by the Cosmetic, Toiletry, and Fragrance Association, (CTFA) as Polyquaternium-16. This material is commercially available from BASF Wyandotte Corp. (Parsippany, N.J., USA) under the LUVIQUAT trade name (e.g. LUVIQUAT FC 370);
copolymers of 1-vinyl-2-pyrrolidine and dimethylaminoethyl methacrylate, referred to in the industry (CTFA) as Polyquaternium-11. This material is available commercially from Gaf Corporation (Wayne, N.J., USA) under the GAFQUAT trade name (e.g., GAFQUAT 755N);
cationic diallyl quaternary ammonium-containing polymers including, for example, dimethyldiallylammonium chloride homopolymer and copolymers of acrylamide and dimethyldiallylammonium chloride, referred to in the industry (CTFA) as Polyquaternium 6 and Polyquaternium 7, respectively;
mineral acid salts of amino-alkyl esters of homo-and co-polymers of unsaturated carboxylic acids having from 3 to 5 carbon atoms, (as described in U.S. Pat. No. 4,009,256);
cationic polyacrylamides(as described in WO95/22311).

Other cationic deposition polymers that can be used include cationic polysaccharide polymers, such as cationic cellulose derivatives, cationic starch derivatives, and cationic guar gum derivatives.

Cationic polysaccharide polymers suitable for use in compositions of the invention include those of the formula:

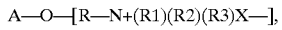

A—O—[R—N+(R1)(R2)(R3)X—], wherein: A is an anhydroglucose residual group, such as a starch or cellulose anhydroglucose residual. R is an alkylene, oxyalkylene, polyoxyalkylene, or hydroxyalkylene group, or combination thereof. R1, R2 and R3 independently represent alkyl, aryl, alkylaryl, arylalkyl, alkoxyalkyl, or alkoxyaryl groups, each group containing up to about 18 carbon atoms. The total number of carbon atoms for each cationic moiety (i.e., the sum of carbon atoms in R1, R2 and R3) is preferably about 20 or less, and X is an anionic counterion.

Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200.

Other suitable cationic polysaccharide polymers include quaternary nitrogen-containing cellulose ethers (e.g. as described in U.S. Pat. No. 3,962,418), and copolymers of etherified cellulose and starch (e.g. as described in U.S. Pat. No. 3,958,581).

A particularly suitable type of cationic polysaccharide polymer that can be used is a cationic guar gum derivative, such as guar hydroxypropyltrimonium chloride (Commercially available from Rhodia (formerly Rhone-Poulenc) in their JAGUAR trademark series).

Examples are JAGUAR C13S, which has a low degree of substitution of the cationic groups and high viscosity. JAGUAR C15, having a moderate degree of substitution and a low viscosity, JAGUAR C17 (high degree of substitution, high viscosity), JAGUAR C16, which is a hydroxypropylated cationic guar derivative containing a low level of substituent groups as well as cationic quaternary ammonium groups, and JAGUAR 162 which is a high transparency, medium viscosity guar having a low degree of substitution.

Preferably the cationic deposition polymer is selected from cationic cellulose and cationic guar derivatives. Particularly preferred deposition polymers are JAGUAR C13S, JAGUAR C15, JAGUAR C17 and JAGUAR C16 and JAGUAR C162.

The cationic deposition polymer will generally be present at levels of from 0.001 to 5%, preferably from about 0.01 to 1%, more preferably from about 0.02% to about 0.5% by weight of the total composition.

Conditioners

Compositions in accordance with the invention may also be formulated as conditioners for the treatment of hair (typically after shampooing) and subsequent rinsing.

Such a conditioner will comprise one or more conditioning surfactants which are cosmetically acceptable and suitable for topical application to the hair.

Suitable conditioning surfactants are selected from cationic surfactants, used singly or in admixture. Examples include quaternary ammonium hydroxides or salts thereof, eg, chlorides.

Suitable cationic surfactants for use in hair conditioners of the invention include cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, and the corresponding hydroxides thereof. Further suitable cationic surfactants include those materials having the CTFA designations Quaternium-5, Quaternium-31 and Quaternium-18. Mixtures of any of the foregoing materials may also be suitable. A particularly useful cationic surfactant for use in hair conditioners of the invention is cetyltrimethylammonium chloride, available commercially, for example as GENAMIN CTACTM, ex Hoechst Celanese.

In conditioners of the invention, the level of cationic surfactant is preferably from 0.01 to 10%, more preferably 0.05 to 5%, most preferably 0.1 to 2% by weight of the composition.

Conditioners of the invention advantageously incorporate a fatty alcohol. The combined use of fatty alcohols and cationic surfactants in conditioning compositions is believed to be especially advantageous, because this leads to the formation of a lamellar phase, in which the cationic surfactant is dispersed.

Representative fatty alcohols comprise from 8 to 22 carbon atoms, more preferably 16 to 20. Examples of suitable fatty alcohols include cetyl alcohol, stearyl alcohol and mixtures thereof. The use of these materials is also advantageous in that they contribute to the overall conditioning properties of compositions of the invention.

The level of fatty alcohol in conditioners of the invention is conveniently from 0.01 to 10%, preferably from 0.1 to 5% by weight of the composition. The weight ratio of cationic surfactant to fatty alcohol is suitably from 10:1 to 1:10, preferably from 4:1 to 1:8, optimally from 1:1 to 1:4.

Hair Styling Gels

Hair treatment compositions in accordance with the invention may also take the form of hair styling gels.

Such a hair styling gel will comprise a water soluble film-forming resin. The resin may either be anionic, nonionic, amphoteric or cationic. Specific resins include polyvinylpyrrolidone (PVP), copolymers of (PVP) and methylmethacrylate, copolymers of PVP and vinyl acetate (VA), polyvinyl alcohol (PVA), copolymers of PVA and crotonic acid, copolymers of PVA and maleic anhydride, hydroxypropyl cellulose, hydroxypropyl guar gum, sodium polystyrene sulfonate, PVP/ethylmethacrylate/methacrylic acid terpolymer, vinyl acetate/crotonic acid/vinyl neodecanoate copolymer, octylacrylamide/acrylates copolymer, monoethyl ester of poly(methyl vinyl ether/maleic acid), and octylacrylamide/acrylate/butylaminoethyl methacrylate copolymers. Mixtures of resins may also be used. PVP and PVP copolymers with other monomers are preferred, e.g. copolymers of polyvinyl pyrrolidone and vinyl acetate, particularly in a 70/30 ratio.

Amounts of the film-forming resin may range from 0.1 to 20%, preferably from 1 to 10%, optimally from 2 to 5% by weight. Small quantities of surfactant ranging anywhere from 0.1 to about 10%, preferably from about 0.1 to about 1%, most preferably about 0.3% by weight may be present in hair styling gels of the invention. The surfactant may be an anionic, nonionic or cationic emulsifier. Particularly preferred are nonionic emulsifiers which are formed from alkoxylation of hydrophobes such as fatty alcohols, fatty acids and phenols.

Hair treatment compositions of this invention may contain any other ingredients normally used in hair treatment formulations. These other ingredients may include viscosity modifiers, preservatives, colouring agents, polyols such as glycerine and polypropylene glycol, chelating agents such as EDTA, antioxidants, fragrances, and sunscreens. Each of these ingredients will be present in an amount effective to accomplish its purpose. Generally these optional ingredients are included individually at a level of up to about 5% by weight of the total composition.

Preferably, compositions of this invention also contain adjuvants suitable for hair care. Generally such ingredients are included individually at a level of up to 2%, preferably up to 1%, by weight of the total composition.

Among suitable hair care adjuvants, are:

(i) natural hair root nutrients, such as amino acids and sugars. Examples of suitable amino acids include arginine, cysteine, glutamine, glutamic acid, isoleucine, leucine, methionine, serine and valine, and/or precursors and derivatives thereof. The amino acids may be added singly, in mixtures, or in the form of peptides, e.g. di- and tripeptides. The amino acids may also be added in the form of a protein hydrolysate, such as a keratin or collagen hydrolysate. Suitable sugars are glucose, dextrose and fructose. These may be added singly or in the form of, e.g. fruit extracts. A particularly preferred combination of natural hair root nutrients for inclusion in compositions of the invention is isoleucine and glucose. A particularly preferred amino acid nutrient is arginine.

(ii) hair fibre benefit agents. Examples are:

ceramides, for moisturising the fibre and maintaining cuticle integrity. Ceramides are available by extraction from natural sources, or as synthetic ceramides and pseudoceramides. A preferred ceramide is Ceramide II, ex Quest. Mixtures of ceramides may also be suitable, such as Ceramides LS, ex Laboratoires Serobiologiques.

The invention will now be further illustrated by the following, non-limiting Examples:

EXAMPLES

In the examples, all percentages are by weight unless indicated otherwise.

Zinc Omadine was obtained from Olin Jaguar deposition polymers were obtained from Rhodia Silicone oils and emulsions (DC2-1391TM and DC2-1699TM) were obtained from Dow Corning Example 1

Preparation of a sheared gel material containing the solid antimicrobial active zinc pyridinethione (ZnPTO).

Agar (Luxura 1253TM, Arthur Branwell, 0.5%) was dispersed in cold water and heated to 95° C. until fully dissolved (until water is clear). Zinc Omadine (2%, contains active zinc pyridinethione) was then added and mixed in. The mixture was introduced into the stirred pot described earlier and illustrated in FIG. 1b (at 85° C.). This was then mixed for 5 mins at 1000 rpm to ensure thorough mixing and then was cooled to 5° C. at 500 rpm over about 30 mins (approximately 2.5° C./min). Phase contrast microscopy images reveal the zinc pyridinethione is substantially all present within the agar sheared gel particles and that this remains the case over at least 4 months.

Figure 3:
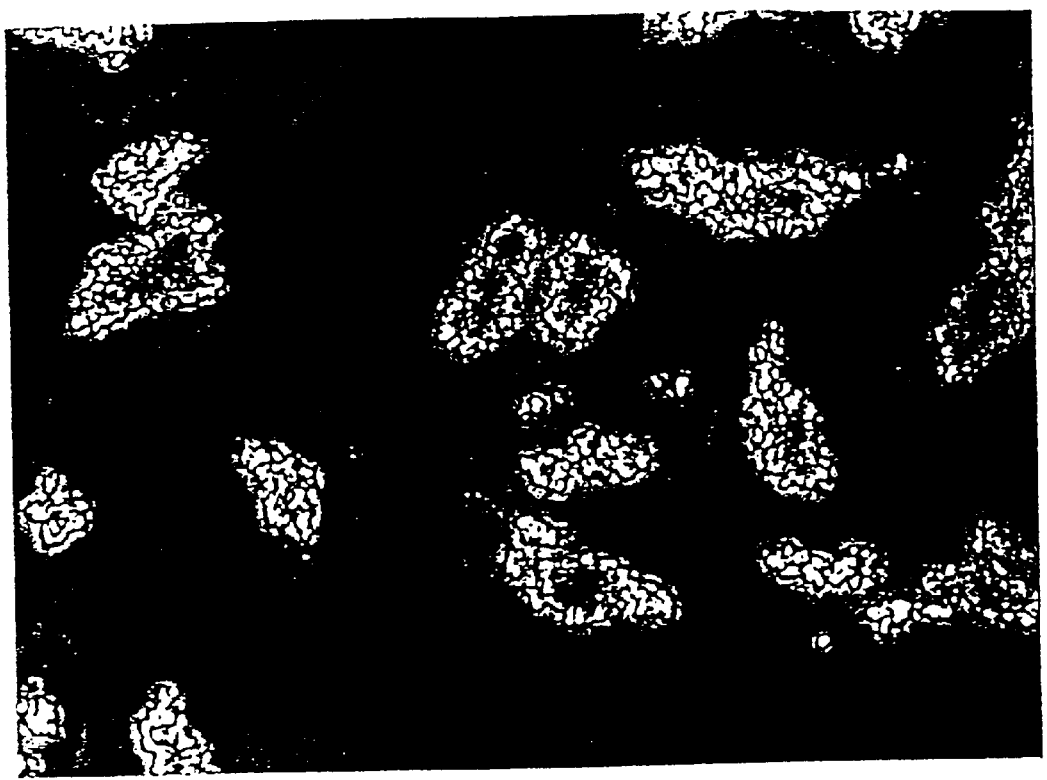

FIG. 3 is a phase contrast light microscopy image showing zinc pyridinethione entrapped within sheared agar gel particles. Note: Image width is 130 $\mu$m.

Example 2

The formulations for the shampoos containing zinc pyridinethione and agar sheared gel particles are given below.

Actual levels of ingredient added are stated, active levels given in brackets.

| Component | Formula 1 Shampoo with 0.5% Luxara 1253 agar (% w/w) | Formula 2 Shampoo with 3.0% Quest LTS agar (% w/w) | Formula 3 Shampoo with 0.5% Quest LTS agar (% w/w) |
|---|---|---|---|
| Sodium laureth 2-ethoxy sulphate (70% active) Primary surfactant | 20 (14) | 20 (14) | 20 (14) |
| Coco-amido propyl betaine (30% active) Co-surfactant | 6.67 (2) | 6.67 (2) | 6.67 (2) |
| Jaguar C13S (1% aqueous solution) Conditioning agent, Deposition aid | 10 (0.1) | 10 (0.1) | 10 (0.1) |
| ZnPTO (48% aqueous solution) Active | 1.048 (0.5) | 1.048 (0.5) | 1.048 (0.5) |
| DMDM Hydantion (100% active liquid) Preservative | 0.3 (0.3) | 0.3 (0.3) | 0.3 (0.3) |
| CI 42051 Blue Dye (0.0144% aqueous solution) Dye | 2.5 (0.0036) | 2.5 (0.0036) | 2.5 (0.0036) |
| Agar shear el (Aqueous solution at 0.5 or 3.0% level) Suspending system | 50 (0.5% Luxara 1253) | 50 (3.0% Quest Deltagar LTS) | 50 (0.5% Quest Deltagar LTS) |
| NaCl (Solid 100%) Viscosity adjuster | To spec | To spec | To spec |
| NaOH/Citric Acid pH adjuster | To spec | To spec | To spec |
| Water Solvent | To 100% | To 100% | To 100% |

Specifications pH adjusted to 5.5 to 6.5 using NaOH/Citric acid Viscosity adjusted to 4500 to 5500 by adding NaCl (usually 1 to 1.5%).

For the comparative tests of Example 3, the same formulations apply for when the zinc pyridinethione is entrapped into the agar sheared gel particles and when it is free amongst the agar sheared gel particles. The formulation is the same, but the manufacture is different. In the latter case, the agar sheared gel is manufactured first and then the zinc pyridinethione is added with the other shampoo ingredients to the sheared gel base during manufacture of the shampoo. In the former case the zinc pyridinethione is coprocessed with the agar sol as detailed in Example 1. The other shampoo ingredients are then added to the filled sheared gel base during manufacture of the shampoo.

Example 3

Deposition Tests
Protocol 2 inch (50.8 mm)/0.25 g switches (virgin, proximal Chinese hair) are washed with 0.03 g of product formulation diluted with 0.27 ml of tap water (room temperature) for 30 s. The switch is then rinsed with warm running tap water (c.a. 35° C.) for 30 s. This wash/rinse phase was then repeated. Five replicates were prepared for each treatment.

Switches were mounted onto a plastic ring such that the maximum amount of hair is exposed to the centre of the ring, the hair on the ring is then covered with a spectroscopically pure 6 $\mu$m polypropylene film to prevent the loss of hairs. The mounted switch was then analysed for elemental zinc on the surface of the hair using X-ray fluorescence. In this technique a beam of X-rays is fired upon the hair surface, electrons are knocked out of low lying energy levels of the atoms on the surface of the hair, electrons from higher energy levels drop down to replace these emitted electrons. This process is accompanied by the emission of electromagnetic radiation (hence the definition fluorescence) in the form of secondary X-rays. The intensity and absolute energy of this emitted radiation gives an indication of the level and identity of the atoms present on the surface of and in the hair.

It is assumed that higher levels of zinc detected on the hair post-wash correspond to ZnPTO deposited on the hair. Hair switches may be dosed with differing levels of ZnPTO and the resultant zinc levels on the surface of the hair measured, thus allowing a calibration (in parts per million) of the level of ZnPTO deposited on the hair.

Performance of Test Products

Figure 4:
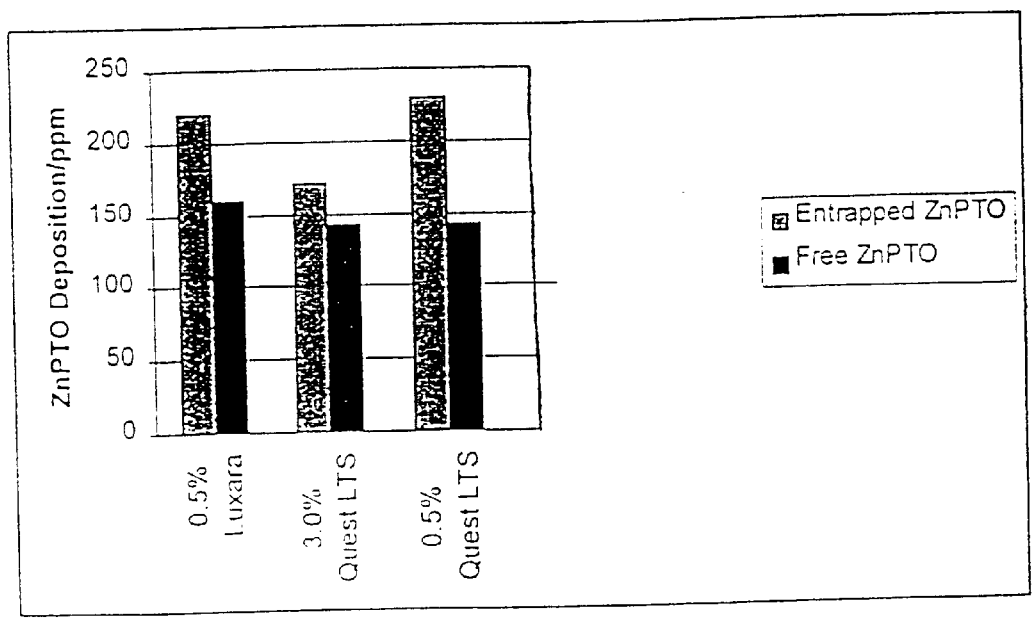

FIG. 4 illustrates the level of ZnPTO deposition of the three test formulae of Example 2, according to the invention, compared to the corresponding formulations in which the ZnPTO is not entrapped in the shear gel particles.

Surprisingly, deposition of ZnPTO from the compositions of the invention with ZnPTO particles entrapped in gel particles of the shear gel, is superior to deposition from the compositions in which ZnPTO is free (i.e. not entrapped in the gel particles) in an otherwise identical composition.

Example 4

Conditioning Shampoo

Preparation of a sheared gel material containing the silicone oil, DC2-1391TM (particle size 40–50 nm).

Agar (Quest Deltagar™, 0.5%) was dispersed in cold water and heated to 95° C. until fully dissolved (until clear). The solution was then cooled to 60° C. before adding the silicone oil (DC2-1391TM, 2% total emulsion, 0.5% active). The oil and the agar sol were mixed together and then introduced into the stirred pot (at 60° C.) as described earlier and illustrated in FIG. 1b. This was then mixed for 5 mins at 1000 rpm to ensure thorough mixing and then was cooled to 5° C. at 500 rpm over about 20 mins (approximately 3° C./min). Transmission electron microscopy images revealed that the silicone oil droplets are associated with the agarose chains within the agar sheared gel particles.

Figure 5:
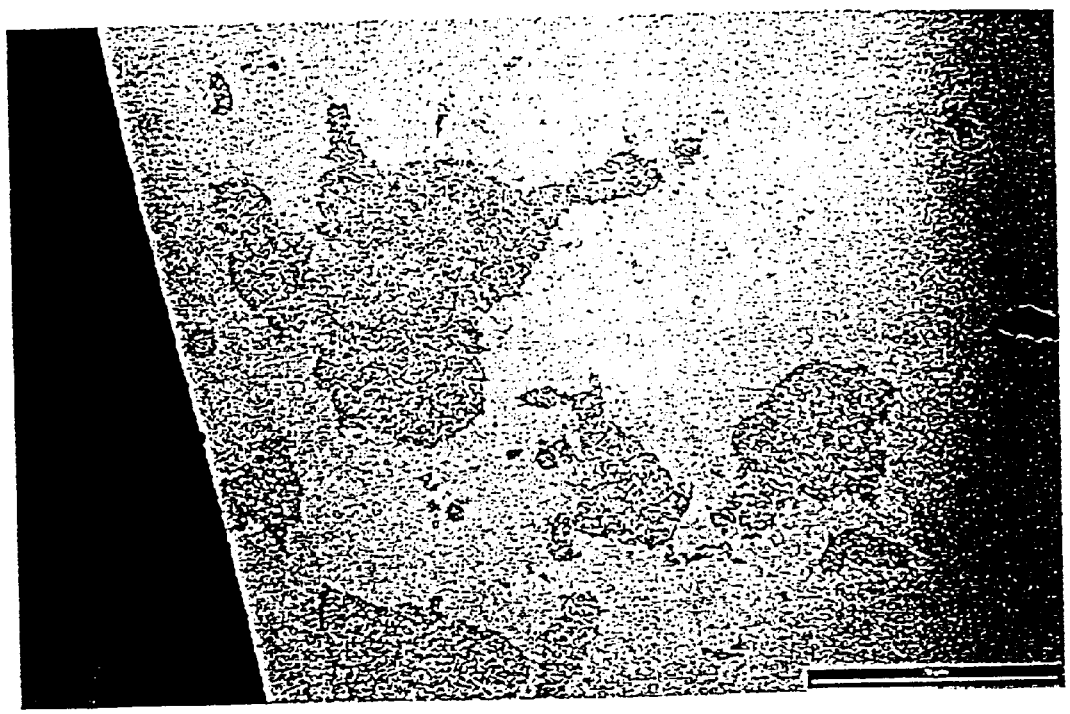

FIG. 5 is a low magnification image of sheared agar gel particles under the Transmission Electron Microscope.

Figure 6:
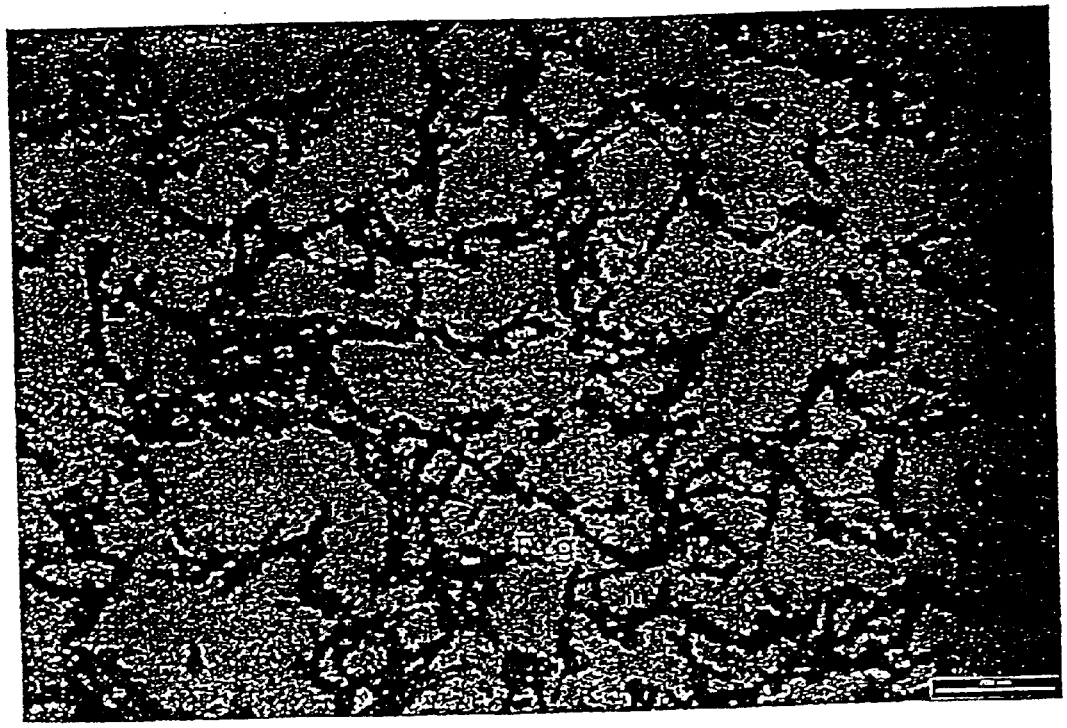

FIG. 6 is a high magnification image showing DC2-1391TM silicone oil droplets within the sheared agar gel particle.

Example 5
Conditioning Shampoo

A typical shampoo formulation is as follows:

% AD is the % of the active
% Comp is the % of the active in the final composition
% W/W is the percentage of the total ingredient added.

| component | % AD | % comp | Function | % w/w |
|---|---|---|---|---|
| Empicol ESB70 | 70 | 14 | Primary surfactant | 20.0 |
| Coco-propylbetaine | 30 | 2 | Co-surfactant | 6.65 |
| Jaguar C13S | 100 | 0.1 | Conditioning agent. Deposition aid | 0.1 |
| Quest Deltagar LTS + DC-1391 | 0.5 | 0.34 | Active & suspending system | 68 |
| Athene 929 | 100 | 0.55 | Perfume | 0.55 |
| Sodium Benzoate | 100 | 0.5 | Preservative | 0.5 |
| Sepicide Ld | 100 | 0.4 | Preservative | 0.4 |
| Timiron MP1001 | 100 | 0.2 | Opacifier | 0.2 |
| Sodium Chloride | 100 | 0.8 | Viscosity adjuster | 0.8 |
| Water | 100 | — | Solvent | To 100 |

The above composition is for 0.5% sheared agar that already contains the silicone oil entrapped within it (0.5% active, 2% total).

Example 6

Many different types of agar sheared gel can be used to entrap actives. If a different particle rheology is required, a different agar type can be employed. This example is the same as Example 1 only the agar employed was Ina Ultra Agar (AX-30) from Ina Food Industry, Japan.

FIG. 6 shows the silicone emulsion, DC2-1669 (Dow Corning) entrapped within rather loosely defined sheared gel particles. The weak gel particles are not as defined as harder agar gels, but the silicone emulsion is closely associated with the polysaccharide chains and is not expelled from the matrix.

Example 7

An example is now given of an alternative polysaccharide to agar. This polysaccharide is K-carrageenan.

K-carrageenan (0.5%, Genugel, X909, Hercules) was added to cold, distilled water, and heated to 60° C. until fully dissolved. Potassium sorbate (0.02%) and potassium chloride (0.22%) was then added and mixed in. The zinc omadine (2% (=1% active ZnPTO)) or silicone emulsion (0.5% active DC2-1669, Dow Corning) was added to the dispersion and the mixture was added to the stirred pot at 60° C. and cooled to 5° C. as detailed in example 1.

Figure 7:
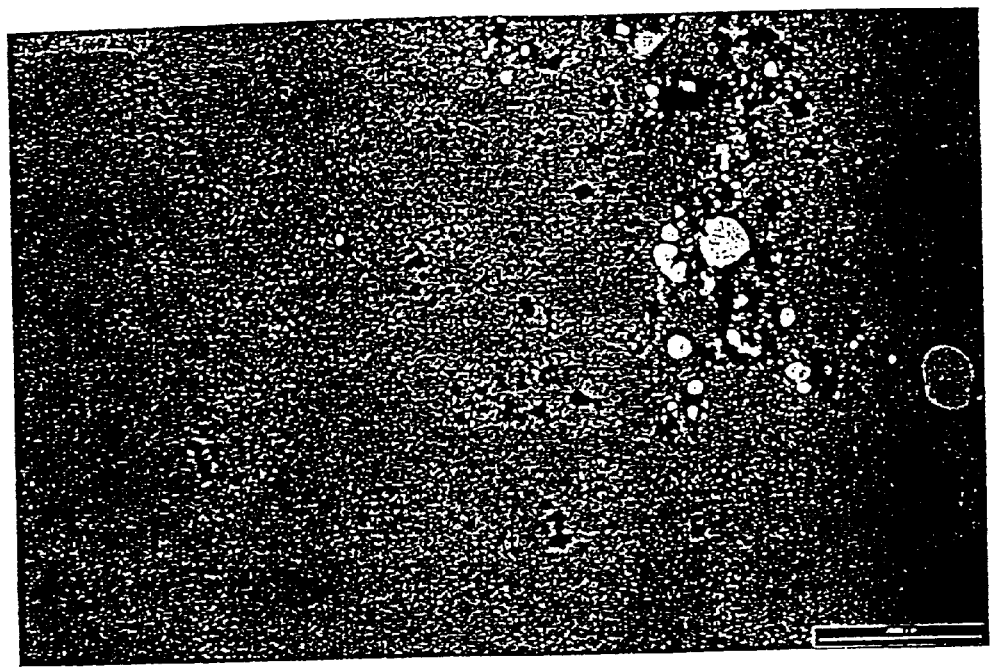
FIG. 7 shows silicone oil entrapped in a low gel strength agar sheared gel.
Figure 8:
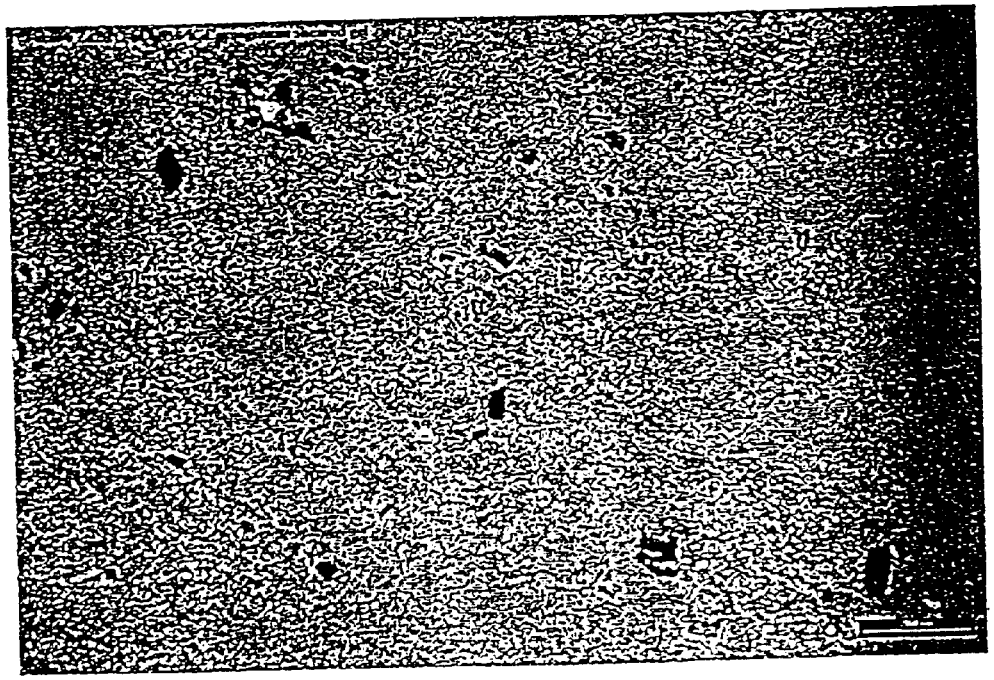
FIG. 8 shows ZnPTO (1%) entrapped within K-carrageenan (0.5%) sheared gel particles.

Micrographs are given of entrapped ZnPTO in K-carrageenan sheared gel particles (FIG. 7) and entrapped silicone emulsion in K-carrageenan sheared gel particles (FIG. 8).

Example 8

An example of a protein sheared gel—whey protein containing oil. Whey protein isolate (400 g, Bipro Davisco foods), was dispersed in cold water (3600 g, room temperature 20° C.), with stirring until all powder had dissolved. This whey solution was then heated to 80° C. while being gently stirred, kept at 80° C. for 30 minutes whilst stirring and then cooled to room temperature.

Sunflower oil (400 g) was added to heated whey solution (3600 g), mixed and then passed once through a homogeniser (Crepaco A3 piston homogeniser) operated at 300 bar to give an emulsion dropsize of $D_{3,2}=0.4\,\mu m$ (measured with Mastersizer from Malvern).

Figure 9:
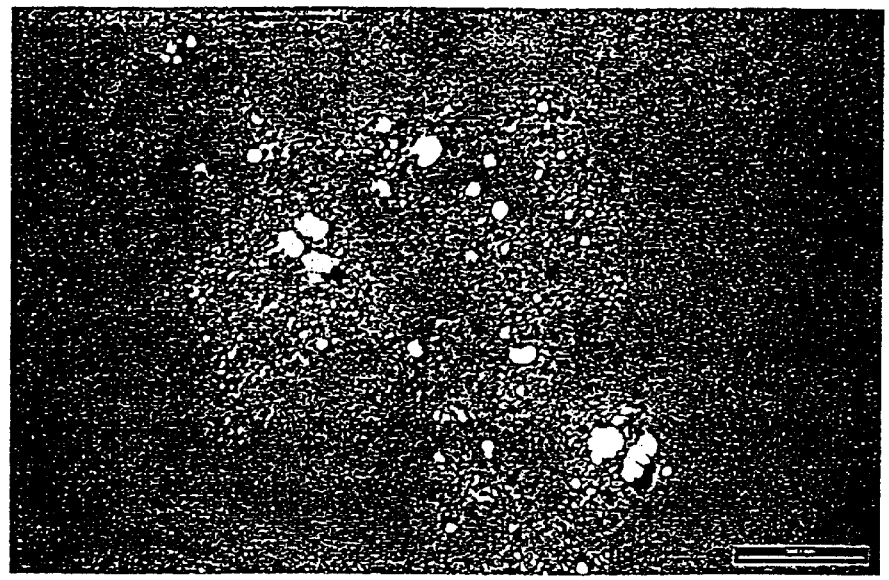
FIG. 9 shows silicone oil (0.5% active, DC2-1669) entrapped within K-carrageenan (0.5%) sheared gel particles.
Figure 10:
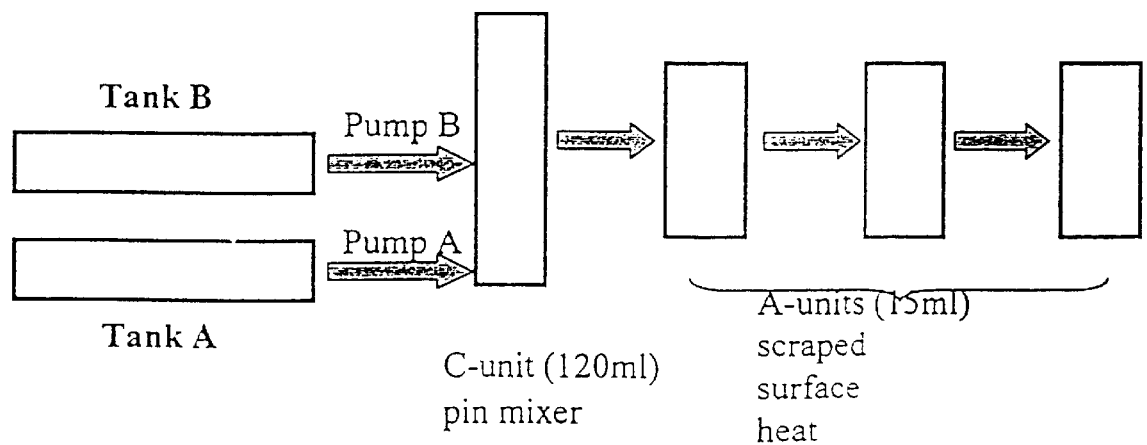
FIG. 10 illustrates a micro-votator line for producing cold set whey sheared gel particles.

This emulsion is then used to make shear whey particles, using a micro-votator line (detailed in FIG. 9). The whey emulsion is placed in tank A, and lactic acid solution (approx. 1.5%) is placed in tank B. The two solutions are introduced into the line by pumping from the tanks into a mixing C unit (a pin mixer of volume 120 ml). The ratio of the mixing and the residence time are controlled by the speed of the pumps. The protein solution was pumped at 42.5 gram/minute and the acid at 10 gram/minute. The tanks are kept at 20° C., and C-unit is at 40° C., and operates at 1400 rpm. The temperature of the solution on exiting the unit is 35° C. The sample is then passed on to a further three A-units operating at 1000 rpm and 20° C., to increase the residence time. The exit temperature from these units is 20° C. The particles are at pH 5.2 and they contain 6.9% protein and 8.1% oil.

What is claimed is:

1. A composition which has a thickened fluid form comprising:
   (i) a first phase, the shear gel phase, comprising at least one polymer which is capable of forming a shear gel, which polymer is present in the composition as a multiplicity of separate gel particles which have been formed by subjecting the polymer to shear while gel formation takes place; and
   (ii) a second phase, the entrapped phase, which is in the form of particles or droplets comprising a hair benefit agent, wherein at least 50 wt % of the hair benefit agent based on its total weight in the composition is entrapped and resides within the gel particles of the shear gel phase, and wherein each gel particle contains on average a plurality of particles or droplets of the hair benefit agent; and
   (III) a third phase, the suspended phase, which is suspended in the shear gel phase wherein the third phase is not entrapped and does not reside within the gel particles of the shear gel phase.

2. The composition according to claim 1 wherein the polymer is a naturally derived polymer selected from the group consisting of polysaccharides, proteins and mixtures thereof.

3. The composition according to claim 1 which is a hair treatment composition.

4. The hair treatment composition according to claim 3 in which the entrapped phase comprises a conditioning agent selected from the group consisting of emulsified silicones and per-alk(en)yl hydrocarbon materials.

5. The hair treatment composition according to claim 3 in which the entrapped phase comprises a solid antimicrobial agent selected from heavy metal salts of pyridinethione, preferably zinc pyridinethione.

6. The composition according to claim 1, wherein the third phase comprises a pearlescing agent selected from the group consisting of polyethylene glycol distearates, ethylene glycol distearates and titanium dioxide coated mica particles, a conditioning agent selected from emulsified silicones and per-alk(en)yl hydrocarbon materials or a solid antimicrobial agent selected from heavy metal salts of pyridinethione, preferably zinc pyridinethione.

7. The hair treatment composition according to claim 3 which is a shampoo composition and which further comprises:
   (a) from 5 to 30% by weight of the total shampoo composition of surfactant, and
   (b) from 0.02% to 0.5% by weight of the total shampoo composition of a cationic deposition polymer.

8. The hair treatment composition according to claim 3 which is a hair conditioner composition and which further comprises:
   (a) from 0.05 to 5% by weight of the total composition of a cationic surfactant, and
   (b) from 0.1 to 5% by weight of the total composition of a fatty alcohol.

9. A process for producing the composition of claim 1 which comprises forming an aqueous solution of the polymer, mixing the solution with particles or droplets of one or more hair benefit agents which are substantially insoluble in the aqueous solution or substantially immiscible with the aqueous solution, and subjecting the solution to gelation while applying shear.

10. The composition according to claim 1 wherein at least 75 wt % of the hair benefit agent based on its total weight in the composition is entrapped and resides within the gel particles of the first phase, and wherein each gel particle contains on average a plurality of particles or droplets of the hair benefit agent.

11. A method of controlling the release and/or the delivery of a hair benefit agent from a hair treatment composition by entrapping at least 50% of the hair benefit agent as a plurality of droplets or particles within gel particles in the composition, wherein said gel particles are formed by subjecting a polymer capable of forming a shear gel to shear white gel formation takes place, and the composition further comprising a third phase, the suspended phase, which is suspended in the shear gel phase wherein the third phase is not entrapped and does not reside within the gel particles of the shear gel phase.

12. The method according to claim 10 wherein the benefit agent is a solid antimicrobial agent.

13. A method of treating hair to improve the delivery of antidandruff benefits by treating the hair with a composition comprising:
   (i) a first phase comprising at least one polymer which is capable of forming a shear gel, which polymer is present in the composition as a multiplicity of separate gel particles which have been formed by subjecting the polymer to shear while gel formation takes place; and
   (ii) a second phase which is in the form of droplets or particles comprising a an antidandruff agent, wherein at least 50 wt % of the antidandruff agent based on its the total weight in the composition is entrapped and resides within the gel particles of the first phase; and
   iii) a third phase, the suspended phase, which is suspended in the shear gel phase wherein the third phase is not entrapped and does not reside within the gel particles of the shear gel phase, and
   wherein each gel particle contains on average a plurality of droplets or particles of the antidandruff agent.

* * * * *